United States Patent

Tanaka

[11] Patent Number: 5,792,093
[45] Date of Patent: Aug. 11, 1998

[54] FOOT SUPPORTER HAVING PROJECTION FOR ACUPRESSURE WHICH ABUTS ON BASE REGION OF TOES WHEN FITTED

[75] Inventor: Nobutaka Tanaka, Daito, Japan

[73] Assignee: Tanaka Planning Corporation, Osaka, Japan

[21] Appl. No.: 807,458

[22] Filed: Feb. 27, 1997

[30] Foreign Application Priority Data

Mar. 19, 1996 [JP] Japan .................. 8-062832

[51] Int. Cl.⁶ .................................................. A61F 5/00
[52] U.S. Cl. ........................ 602/63; 602/62; 602/30
[58] Field of Search .......................... 602/5, 12, 23, 602/27–30, 61, 63, 65, 66; 606/204, 201; 128/882, 907; 336/43, 44; 601/133, 134, 151

[56] References Cited

U.S. PATENT DOCUMENTS

| | | | |
|---|---|---|---|
| 1,639,198 | 8/1927 | Pease | 602/66 X |
| 3,703,171 | 11/1972 | Schiavitto | 602/63 X |
| 4,813,162 | 3/1989 | Harris | 36/43 X |
| 5,140,978 | 8/1992 | Siminger | 601/133 X |
| 5,282,782 | 2/1994 | Kasahara | 602/5 X |
| 5,290,307 | 3/1994 | Choy | 606/204 |
| 5,403,265 | 4/1995 | Berguer | 601/151 |
| 5,445,598 | 8/1995 | Nguyen-Senderowicz | 602/65 |
| 5,533,399 | 7/1996 | Strong | 36/44 X |
| 5,617,745 | 4/1997 | Della Corte et al. | 602/65 X |

OTHER PUBLICATIONS

Spiral Taping, by Nobutaka Tanaka, published Nov. 1, 1991 (Japan), pp. 1–163.

*Primary Examiner*—Lynne A. Reichard
*Assistant Examiner*—Denise Pothier
*Attorney, Agent, or Firm*—Rabin & Champagne, P.C.

[57] ABSTRACT

A foot supporter body is formed into a cylindrical shape using cloth having excellent elasticity and it has an approximately X-shaped acupressure projection on its inner side including first to fourth linear ribs extending in four directions from the center. The acupressure projection is formed in a symmetrical shape on the right and left sides of the center. When this foot supporter is fitted on the foot in the region somewhat back from the base region of the toes, the acupressure projection stimulates the surface of the foot to produce the effect of treating hallux valgus and the like and reducing the pain in the sole of foot caused by the this problem.

15 Claims, 6 Drawing Sheets

FOOT SUPPORTER HAVING PROJECTION FOR ACUPRESSURE WHICH ABUTS ON BASE REGION OF TOES WHEN FITTED

BACKGROUND OF THE INVENTION

1. Field of the Invention

The present invention relates to supporters, and particularly to a foot supporter for treating hallux valgus and minimus valgus and for reducing the pain due to these troubles, which can also be used to reduce pain in the sole of the foot caused when exercising, and for other purposes.

2. Description of the Background Art

If hallux valgus, in which the base of the big toe (hallux) of the foot outwardly projects, occurs, the projecting part of the toe is pressed against a shoe, for example. This may cause pain not only in that region but also in a region extending to the ankle or to the knee. The same is true in the case of minimus valgus in which the base of the little toe (minimus) outwardly protrudes.

The technique of so-called taping for treating hallux valgus and the like, and reduction in the accompanying pain, by sticking adhesive tapes on the diseased part is known, which is practiced in an osteopath's office, for example.

FIGS. 8A and 8B shows a taping technique applied to the region of the base of the toes. In FIG. 8(A) and (B), adhesive tapes 9 having a width of about 3 mm are stuck on the instep of the foot to treat hallux valgus and the pain in the sole of the foot due to this trouble. For example, in FIG. 8(A), the adhesive tapes 9 are attached in an intersecting manner on the region from the upper surface of the fourth MP joint 804, which is the joint between the fourth proximal phalanx 84 constituting the fourth toe and the corresponding fourth metatarsal 88, to the outer side of the front end of the first metatarsal 85 and on the region from the first MP joint 801, which is the joint between the first metatarsal 85 and the first proximal phalanx 81, to the vicinity of the front end of the fifth metatarsal 89. Adhesive tapes fastened in this manner, in the manner as shown in FIG. 8(A) and (B) stimulate the region where they adhere, to provide an acupressure (shiatsu) effect for treating hallux valgus or minimus valgus. Further, the tapes also reduce the pain in the sole of the foot caused by this trouble (For example, refer to "Spiral Taping" by Nobutaka Tanaka, published on Nov. 1, 1991 in Japan.).

In the aforementioned taping technique, however, the adhesive tapes are difficult to handle because of their adhesiveness. Furthermore, the adhesive may cause a rash on the skin, depending on the patient. Moveover, since the adhesive tapes removed from the body can not be reused, they must be discarded. Accordingly, it is necessary to prepare and use new adhesive tapes every time the treatment is performed.

SUMMARY OF THE INVENTION

An object of the present invention is to provide a foot supporter which can avoid the troublesome work of sticking difficult-to-handle adhesive tape on the body.

Another object of the present invention is to provide a foot supporter which eliminates the possibility of a rash on the skin.

Still another object of the present invention is to provide a foot supporter which can be freely attached on and detached from the body so that it can be repeatedly used.

In order to achieve the above objects, a health promoting implement according to one aspect of the present invention is directed to a foot supporter which includes a cylindrical part which surrounds the end of the foot, wherein an approximately X-shaped projection for acupressure is formed on the inner surface of the cylindrical part nearly symmetrically on the right and the left with respect to the center which approximately corresponds to the center in the right and left directions on the upper surface of the foot when fitted.

In use, the cylindrical part of the supporter is fitted around the region near the end of the foot. It is fitted such that the center part of the acupressure projection on the inner side of the foot supporter is located approximately in the center in the right and left directions on the upper surface of the foot. Then the top region of the acupressure projection abuts against the base region of the toes to stimulate that region, thereby effectively treating hallux valgus and minimus valgus and lightening the pain in the sole of the foot caused by the disease.

The acupressure projection may have its four ends extending to the sole of the foot, or the overall dimension of the acupressure projection, in a direction of a center axis of the cylindrical part may be about 40 mm, i.e., the ends are set apart by about 40 mm. Then the acupressure projection is shaped like the adhesive tapes stuck as shown in the conventional example depicted in FIG. 8, thus providing further remarkable treatment effect.

According to another aspect of the present invention, the raised height of the acupressure projection is uniform in the entire area and the entire acupressure projection almost uniformly stimulates the surface of the body. This prevents strong stimulation locally applied to a part of the foot, as would be caused in the case of an acupressure projection having a partially raised portion.

According to still another aspect of the present invention, the acupressure projection is separated at the center in the direction perpendicular to the center axis of the cylindrical part. Then the center part will not protrude higher than the other region to locally apply strong stimulation to a part of the foot.

According to still another aspect of the present invention, the end of the cylindrical part is closed. When it is fitted around the end region of the foot from its opening, the closed end of the cylindrical part abuts on the tip of the toe. Hence, the acupressure projection is naturally positioned in the position where it abuts on the foot.

According to still another aspect of the present invention, the entire form of the foot supporter is shaped like a sock capable of surrounding the entire area from the tip of the toe to the ankle. Therefore, the foot supporter will not get out of its proper position even when putting on/taking off a shoe with the supporter fitted on the foot.

As has been described above, according to the present invention, a foot supporter is provided which can apply effective stimulation for hallux valgus and minimus valgus and to lighten a pain caused by the trouble as it is just worn on the foot, thereby eliminating the necessity of the troublesome work of sticking the difficult-to-handle adhesive tapes on the body as has been necessary in the aforementioned taping.

Furthermore, unlike the aforementioned conventional taping procedure, the present invention uses no tape, and therefore it eliminates the possibility of a rash on the skin due to the adhesive agent.

Furthermore, since the foot supporter according to the exemplary aspect of the present invention can be freely fitted on and removed from the foot, it can be repeatedly used, unlike the aforementioned taping technique in which the adhesive tapes removed from the body have to be discarded.

Particularly, according to the exemplary aspect of the present invention, the foot supporter has its end closed. Accordingly, when it is fitted on the foot, the acupressure projection is naturally positioned in the longitudinal (front-back) direction on the foot, thus enabling proper stimulation to the part to be stimulated by the acupressure projection.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
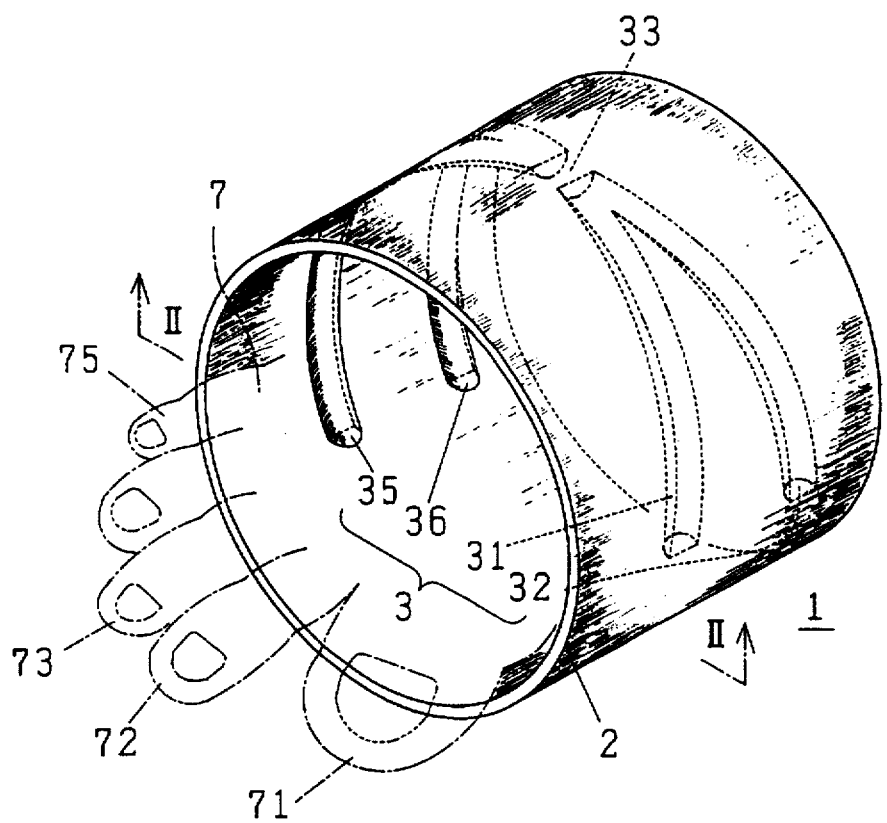
FIG. 1 is a perspective view of a foot supporter according to a first embodiment of the present invention.
Figure 2:
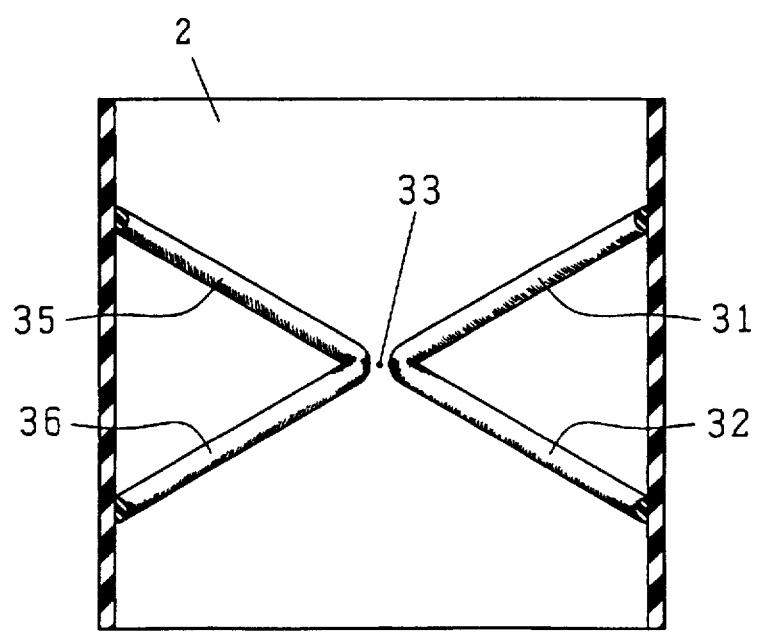
FIG. 2 is a cross-sectional view taken along the line II—II in FIG. 1.

FIG. 1 is a perspective view of a foot supporter 1 according to a first embodiment of the present invention. FIG. 2 is a cross-sectional view taken along the line II—II.

Referring to the figures, a supporter body 2 is formed into a cylindrical form using cloth having excellent elasticity. It has an approximately X-shaped acupressure ("Shiatsu" in Japanese) projection (raised part) 3, and includes first to fourth linear ribs 31, 32, 35 and 36 formed on its inner side. The ribs 31, 32, 35 and 36 extend in four directions from a common center 33. In this embodiment, the acupressure projection 3 is symmetrically formed in the right and left direction (in a direction essentially perpendicular to a center axis of the cylindrical supporter body 2) about the center 33. The first to fourth linear ribs 31, 32, 35 and 36 may be connected at the center 33. However, the acupressure projection 3 is still approximately symmetrical on the right and left sides with respect to the center 33.

The space between the lower ends of the first and second linear ribs 31 and 32 and the space between the lower ends of the third and fourth linear ribs 35 and 36 (i.e., overall dimension in the longitudinal (front-back) direction of the acupressure projection 3) are about 35 to 40 mm in this embodiment. In this embodiment, the height of the first to fourth linear ribs 31, 32, 35 and 36 from the supporter body 2 is about 1 mm in the entire area and the width of the first to fourth linear ribs 31, 32, 35 and 36 is about 5 mm. The lower ends of the first to fourth linear ribs 31, 32, 35 and 36 extend in a direction normal to the longitudinal direction of the supporter body 2. The lower ends of the first and second linear ribs 31 and 32 are parallel to each other, and the lower ends of the third and fourth linear ribs 35 and 36 are also parallel to each other.

Figure 3:
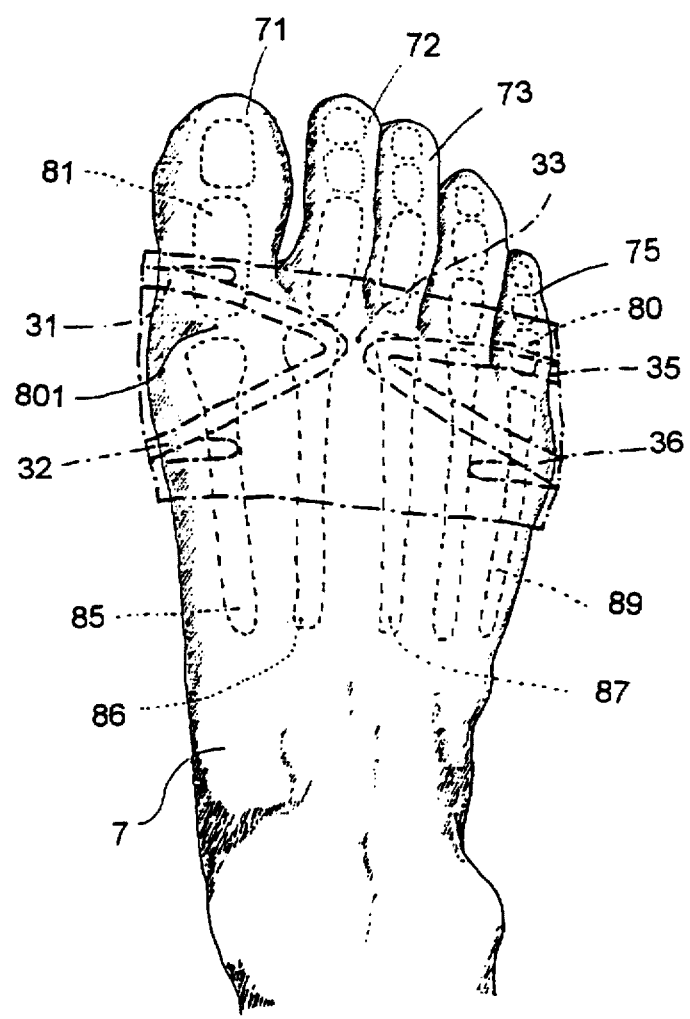
FIG. 3 is a diagram showing the positional relation between the acupressure projection formed on the foot supporter of FIG. 1 and the foot.

As shown in FIG. 1 and FIG. 3, the third linear rib 35 is formed from the sole side of the fifth proximal phalanx 80, forming the base region of the little toe 75 of the foot 7, to connect to the center 33 located back from the boundary between the base of the second toe 72 and that of the third toe 73 (in the vicinity of the boundary between the front ends of the second metatarsal 86 and the third metatarsal 87.) The second linear rib 32 is formed from the center 33 to the sole of the foot via the outer side of the first metatarsal 85. The first linear rib 31 is formed from the sole under the first proximal phalanx 81 forming the base of the big toe 71 to the center 33 via the side of the first MP joint 801. The fourth linear rib 36 is formed from the center 33 to the sole via the side of the fifth metatarsal 89. Accordingly, when the first to fourth linear ribs 31, 32, 35 and 36 come in contact with the foot in the aforementioned manner, the center 33 at which the first to fourth linear ribs 31, 32, 35 and 36 gather is located in the vicinity of the boundary between the ends of the second metatarsal 86 and the third metatarsal 87.

Figure 4:
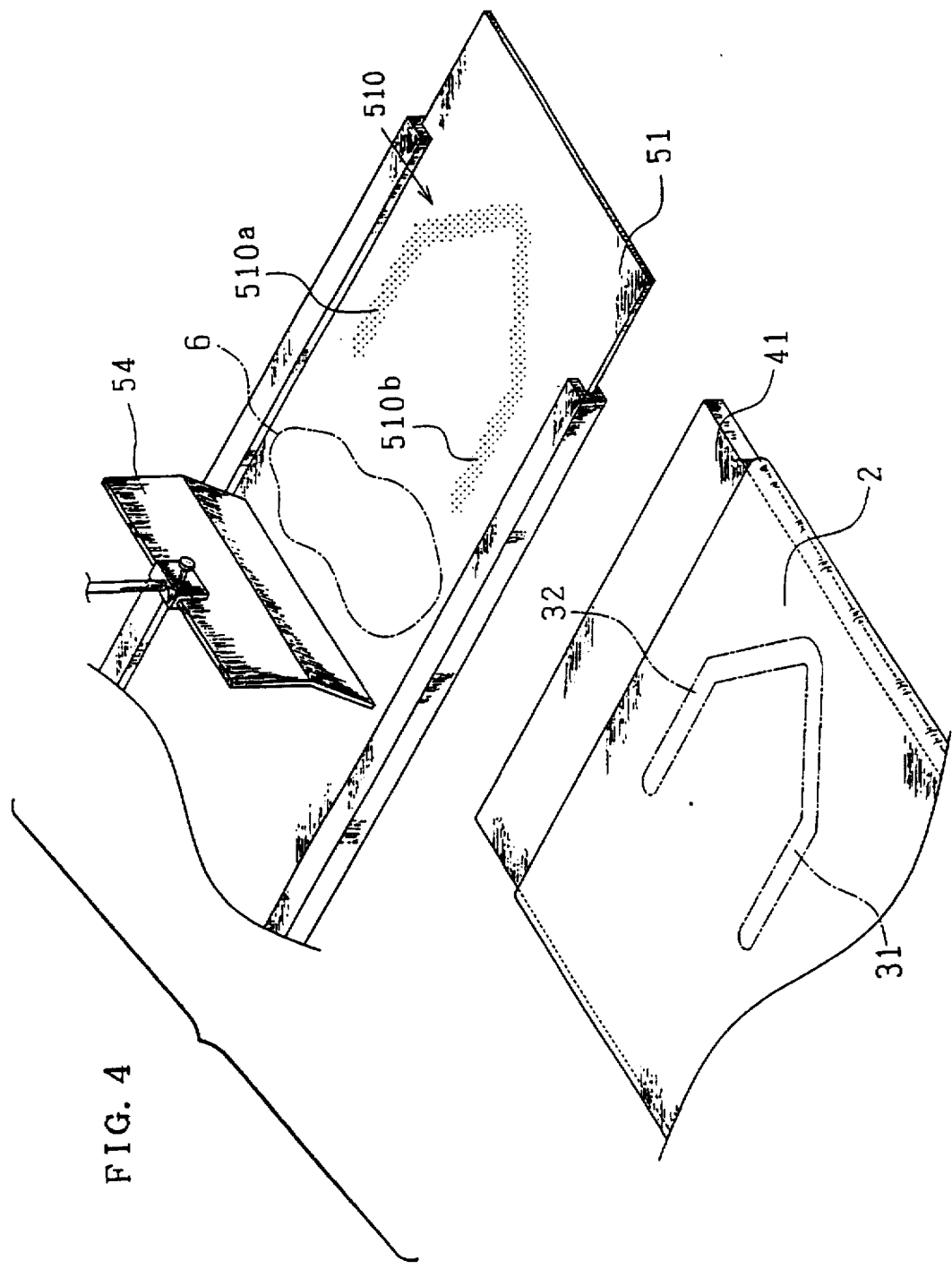
FIG. 4 is a diagram illustrating the process of forming the acupressure projection 3 when manufacturing the foot supporter of FIG. 1.

The acupressure projection 3 is formed on the inner surface of the supporter body 2 by using the apparatus shown in FIG. 4.

The apparatus has a plate-like arm 41 for holding the supporter body 2, a plate 51 having a group of fine holes 510 formed in an approximately V-shaped, and a spatula 54 which slides on the upper surface of the plate 51. The legs 510a and 510b of the V-shaped region of the fine holes 510 are parallel to each other.

When forming the acupressure projection 3 on the supporter body 2 using the aforementioned apparatus, the supporter 2 is fitted around the plate-like arm 41 turned inside out, and silicone 6 in paste form is supplied on the plate 51 in front of the spatula 54. Next, the plate-like arm 41 is moved to under the plate 51 and the supporter body 2 is brought into contact with the back side of the group of fine holes 510. When in this condition, the spatula 54 is moved to press out the paste-like silicone 6 through the fine holes 510 and onto the supporter body 2, so that the silicone 6 attaches on the surface of the supporter body 2. The silicone rubber is thus applied to form the formation of the first and second linear ribs 31 and 32, as shown by the phantom line.

Figure 7:
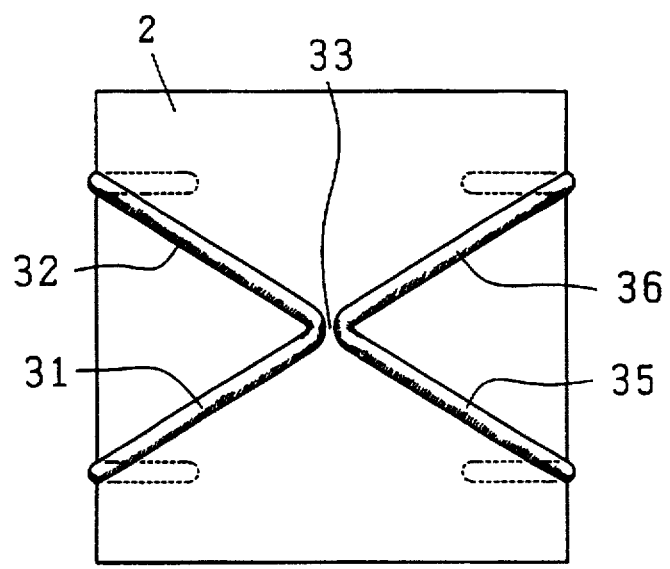
FIG. 7 is a cross-sectional view showing a modification of the acupressure projection formed by the apparatus shown in FIG. 4.

Next, the supporter body 2 is removed from the plate-like arm 41, and then the supporter 2 is turned so that the surface supplied with the silicone 6 faces down. That is to say, the supporter body 2 is turned by 180 degrees. Then the supporter body 2 is again fitted around the plate-like arm 41, and the silicone 6 is applied as stated above. Then, as shown in FIG. 7, the silicone 6 is applied so that the first to fourth linear ribs 31, 32, 35 and 36 are formed. Subsequently, the silicone 6 is heated and dried to form the acupressure projection 3 having proper elasticity on the supporter body 2. The supporter body 2 is then turned right-side in to complete the foot supporter shown in FIG. 1.

Figure 8A:
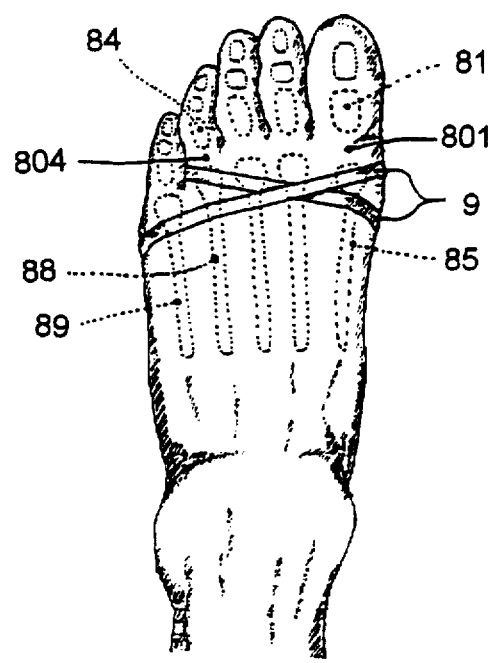
FIGS. 8A and 8B are diagrams illustrating conventional examples of a taping technique applied on the foot.
Figure 8B:
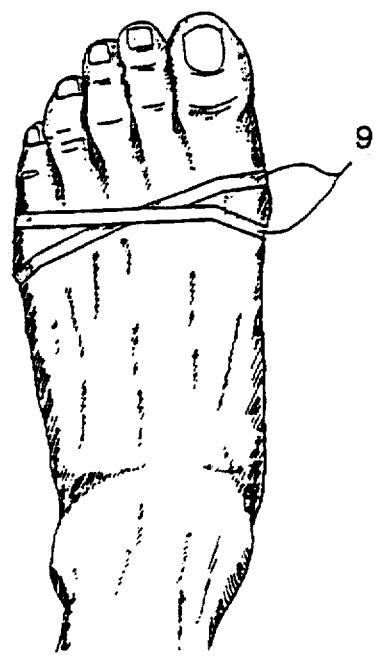

When the foot supporter is fitted on the foot 7 somewhat back from the base region of the toes as shown in FIG. 3, the elasticity of the supporter body 2 presses the first to fourth linear ribs 31, 32, 35 and 36 against the surface of the foot 7 in the above-stated positions. That is to say, they stimulate the surface of the foot 7 like the aforementioned adhesive tapes 9 shown in FIG. 8(B). This provides treatment for hallux valgus, and minimus valgus and lightens the pain in the sole of the foot and so forth caused by the trouble.

Figure 5:
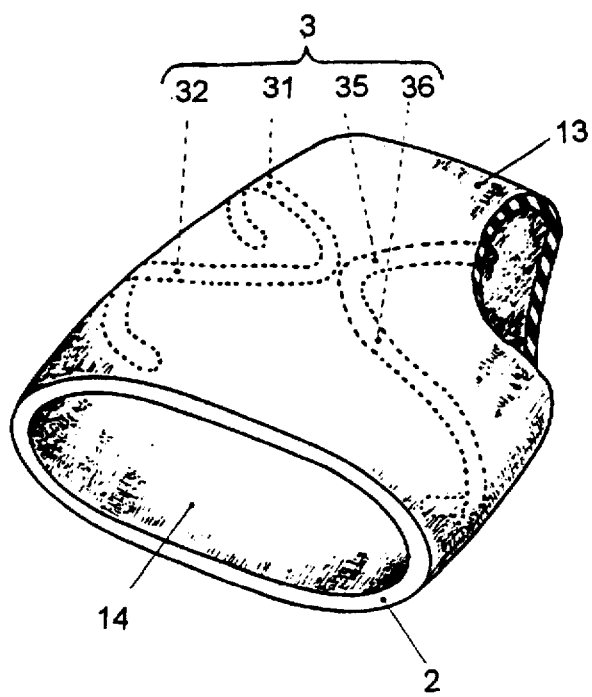
FIG. 5 is a partially broken perspective view of a foot supporter according to a second embodiment.

FIG. 5 is a partially broken perspective view of a foot supporter according to a second embodiment of the present invention.

The supporter body 2 is formed into cylindrical form having its end closed. It has the first to fourth linear ribs 31, 32, 35 and 36 on its inner side, formed in the same way as those on the foot supporter of the first embodiment. That is to say, the acupressure projection 3 of FIG. 5 has the same structure as that adopted in the first embodiment described above.

When the foot supporter 1 is fitted around the foot 7 from the opening 14, the closed end 13 of the foot supporter 1 abuts on the tip of the toe of the foot 7, so that the acupressure projection 3 is naturally positioned in the proper position on the foot 7.

Figure 6:
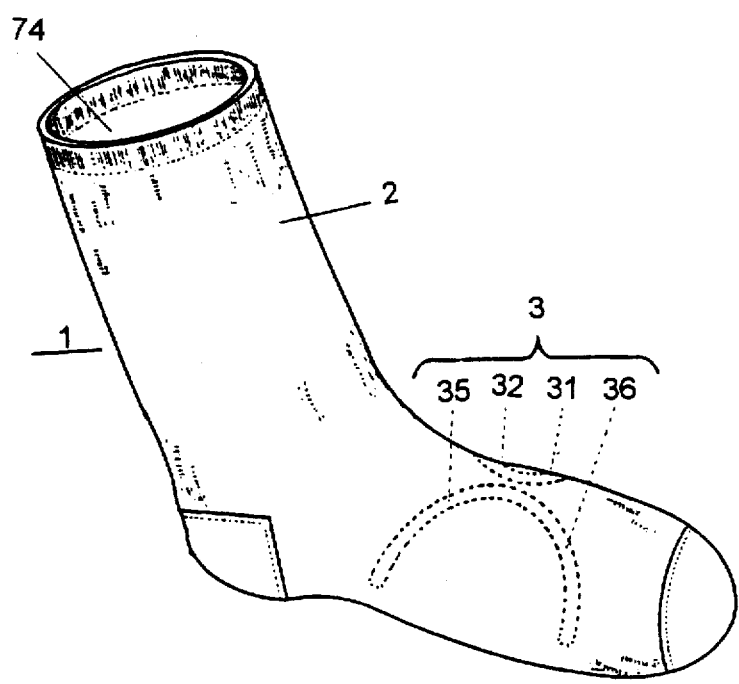
FIG. 6 is a perspective view of a foot supporter according to a third embodiment of the present invention.

FIG. 6 is an external perspective view of a foot supporter according to a third embodiment of the present invention.

The supporter body 2 is in the form of a sock, which surrounds the entire area from the region above the ankle to the tip of the toes. Like the foot supporters according to the above-described embodiments, it has the acupressure projection 3 including the first to fourth linear ribs 31, 32, 35 and 36 formed on the inner upper surface, near the end of the sock. The structure of the acupressure projection 3 is the same as that adopted in the foot supporters of the aforementioned embodiments.

In this embodiment, since the foot supporter is in the form of a sock, wearing it positions the acupressure projection 3 in the proper position on the surface of the foot 7. Furthermore, the foot supporter 1 will not come off the foot 7 even when putting on and taking off a shoe.

While the invention has been described in detail, the foregoing description is in all aspects illustrative and not restrictive. It is understood that numerous other modifications and variations can be devised without departing from the scope of the invention.

I claim:

1. An acupressure device for a foot, comprising:

a body having at least a portion with an essentially cylindrical shape adapted to surround an end of a foot; and a plurality of ribs collectively arranged approximately in an X-shape on an inner surface of the portion of said body, each rib having a non-planar surface projecting away from said inner surface so that when said body is located on the foot, the non-planar surfaces of said ribs are in contact with an upper surface of the foot.

2. The acupressure device of claim 1, wherein said plurality of ribs comprise at least four ribs essentially symmetrically arranged, whereby when said body is located on the foot, a center of the X-shape is positioned over a center of the upper surface of the foot with two of said ribs being arranged on a right side of the foot, and two of said ribs being arranged on a left side of the foot.

3. The acupressure device of claim 2, wherein each rib extends around the portion of said body so that when said body is located on the foot, each rib extends from the upper surface of the foot, to a sole of the foot.

4. The acupressure device of claim 3, wherein each rib has an end, with each respective end being separated from an adjacent end located on a same side of the foot by a distance of about 40 mm.

5. The acupressure device of claim 3, wherein each rib has a uniform height over its entire length.

6. The acupressure device of claim 3, wherein said ribs arranged to be on the right side of the foot are separated, at the center of the X-shape, from said ribs arranged to be on the left side of the foot.

7. The acupressure device of claim 3, wherein an end of the portion of said body is closed.

8. The acupressure device of claim 3, wherein said body is sock-shaped, so that when said body is located on the foot, the foot is surrounded by said body from a tip of a toe of the foot to an ankle.

9. The acupressure device of claim 2, wherein each rib has an end, with each respective end being separated from an adjacent end located on a same side of the foot by a distance of about 40 mm.

10. The acupressure device of claim 2, wherein each rib has a uniform height over its entire length.

11. The acupressure device of claim 2, wherein said ribs arranged to be on the right side of the foot are separated, at the center of the X-shape, from said ribs arranged to be on the left side of the foot.

12. The acupressure device of claim 1, wherein an end of the portion of said body is closed.

13. The acupressure device of claim 1, wherein said body is sock-shaped, so that when said body is located on the foot, the foot is surrounded by said body from a tip of a toe of the foot to an ankle.

14. A method of treating hallux valgus and minimus valgus, which comprises utilizing the acupressure device of claim 1.

15. An acupressure device for a foot, comprising:

a body having at least a portion adapted to surround an end of a foot; and a plurality of ribs collectively arranged approximately in an x-shape on an inner surface of the portion of said body, each rib having a height to width ratio of about 1:5, so that when said body is located on the foot, said ribs are urged against an upper surface of the foot to stimulate the foot for treating hallux valgus and minimus valgus.

* * * * *